United States Patent
Laird et al.

(10) Patent No.: US 6,794,142 B2
(45) Date of Patent: Sep. 21, 2004

(54) AMPLIFICATION USING MODIFIED PRIMERS

(75) Inventors: Walter J. Laird, Pinole, CA (US); John T. Niemiec, San Leandro, CA (US)

(73) Assignee: Roche Molecular Systems, Inc., Alameda, CA (US)

(*) Notice: Subject to any disclaimer, the term of this patent is extended or adjusted under 35 U.S.C. 154(b) by 0 days.

(21) Appl. No.: 10/083,233

(22) Filed: Oct. 24, 2001

(65) Prior Publication Data

US 2003/0044817 A1 Mar. 6, 2003

Related U.S. Application Data

(60) Provisional application No. 60/243,182, filed on Oct. 25, 2000.

(51) Int. Cl.[7] ............................ C12P 1/68; C07H 21/04; C07H 21/02; C07H 19/20
(52) U.S. Cl. ......................... 435/6; 435/91.2; 536/24.3; 536/24.33; 536/23.1; 536/23.3; 536/25.31; 536/25.32; 536/26.71
(58) Field of Search ..................... 435/6, 91.2, 810; 536/24.3, 24.33, 23.1, 25.31, 25.32, 26.71

(56) References Cited

U.S. PATENT DOCUMENTS 6,001,611 A * 12/1999 Will ....................... 435/91.2

2002/0103353 A1   8/2002 Kurane et al. ............... 435/6
2002/0172962 A1 * 11/2002 Gold et al. ................... 435/6

FOREIGN PATENT DOCUMENTS

GB  WO 00/56747  *  9/2000  ........... C07H/19/04
WO  WO 98/02582     1/1998  ............. C12Q/1/68

OTHER PUBLICATIONS

Aurup, H., et al., 1994, "Oligonucleotide duplexes containing 2'–amino–2'–deoxycytidines: thermal stability and chemical reactivity", *Nucleic Acids Research*, 22(1):20–24.

Cummins, L., et al., 1995, "Characterization of fully 2'–modified oligoribonucleotide hetero– and homoduplex hybridization and nuclease sensitivity", *Nucleic Acids Research*, 23(11):2019–2024.

Wilds, C., et al., 2000, "2'–Deoxy–2'fluoro–β–D–arabinonucleosides and Oligonucleotides (2'F–ANA): Synthesis and physicochemical studies", *Nucleic Acids Research*, 28(18):3625–3635.

* cited by examiner

Primary Examiner—Kenneth R. Horlick
Assistant Examiner—Joyce Tung
(74) Attorney, Agent, or Firm—Charles M. Doyle; Townsend and Townsend and Crew LLP

(57) ABSTRACT

The present invention provides modified primers for use in the amplification of a nucleic acid sequence. Amplifications carried out using the modified primers result in less template-independent non-specific product (primer dimer) compared to amplifications carried out using unmodified primers.

20 Claims, No Drawings

SEQUENCE LISTING

<160> NUMBER OF SEQ ID NOS: 4

<210> SEQ ID NO 1
<211> LENGTH: 29
<212> TYPE: DNA
<213> ORGANISM: Artificial
<220> FEATURE:
<223> OTHER INFORMATION: Description of Artificial Sequence:
      Amplification primer

<400> SEQUENCE: 1
agtgggggga catcaagcag ccatgcaaa                                    29

-continued

```
<210> SEQ ID NO 2
<211> LENGTH: 30
<212> TYPE: DNA
<213> ORGANISM: Artificial
<220> FEATURE:
<223> OTHER INFORMATION: Description of Artificial Sequence:
      Amplification primer

<400> SEQUENCE: 2
agtgggggga catcaagcag ccatgcaaat                                        30

<210> SEQ ID NO 3
<211> LENGTH: 31
<212> TYPE: DNA
<213> ORGANISM: Artificial
<220> FEATURE:
<221> NAME/KEY: misc_feature
<223> OTHER INFORMATION: Description of Artificial Sequence:
      Amplification primer

<400> SEQUENCE: 3
agtgggggga catcaagcag ccatgcaaat g                                      31

<210> SEQ ID NO 4
<211> LENGTH: 30
<212> TYPE: DNA
<213> ORGANISM: Artificial
<220> FEATURE:
<223> OTHER INFORMATION: Description of Artificial Sequence:
      Amplification primer

<400> SEQUENCE: 4
ggtactagta gttcctgcta tgtcacttcc                                        30
```

AMPLIFICATION USING MODIFIED PRIMERS

This application claims the benefit of priority under 35 U.S.C. §119 of co-pending provisional application no. 60/243,182 filed on Oct. 25, 2000, the content of which is hereby incorporated in its entirety.

BACKGROUND OF THE INVENTION

1. Field of the Invention

The present invention relates to the field of molecular biology and nucleic acid chemistry. More specifically, it relates to methods and reagents for improving nucleic acid amplification reactions. The invention therefore has applications in any field in which nucleic acid amplification is used.

2. Description of Related Art

The invention of the polymerase chain reaction (PCR) made possible the in vitro amplification of nucleic acid sequences. PCR is described in U.S. Pat. Nos. 4,683,195; 4,683,202; and 4,965,188; Saiki et al., 1985, Science 230:1350–1354; Mullis et al., 1986, Cold Springs Harbor Symp. Quant. Biol. 51:263–273; and Mullis and Faloona, 1987, Methods Enzymol. 155:335–350; each of which is incorporated herein by reference. The development and application of PCR are described extensively in the literature. For example, a range of PCR-related topics are discussed in PCR Technology—principles and applications for DNA amplification, 1989, (ed. H. A. Erlich) Stockton Press, New York; PCR Protocols: A guide to methods and applications, 1990, (ed. M. A. Innis et al.) Academic Press, San Diego; and PCR Strategies, 1995, (ed. M. A. Innis et al.) Academic Press, San Diego; each of which is incorporated herein by reference. Commercial vendors, such as Applied Biosystems (Foster City, Calif.), market PCR reagents and publish PCR protocols.

Since the original publication of nucleic acid amplification, various primer-based nucleic acid amplification methods have been described including, but not limited to, the strand displacement assay (Walker et al., 1992, Proc. Natl. Acad. Sci. USA 89:392–396, Walker et al. 1992, Nucleic Acids Res. 20:1691–1696, and U.S. Pat. No. 5,455, 166) and the transcription-based amplification systems, including the methods described in U.S. Pat. Nos. 5,437, 990; 5,409,818; and 5,399,491; the transcription amplification system (TAS) (Kwoh et al., 1989, Proc. Natl. Acad. Sci. USA 86:1173–1177); and self-sustained sequence replication (3SR) (Guatelli et al., 1990, Proc. Natl. Acad. Sci. USA 87:1874–1878 and WO 92/08800). All of the above references are incorporated herein by reference. A survey of amplification systems is provided in Abramson and Myers, 1993, Current Opinion in Biotechnology 4:41–47, incorporated herein by reference.

Specificity of primer-based amplification reactions largely depends on the specificity of primer hybridization and extension. Under the elevated temperatures used in a typical amplification, the primers hybridize only to the intended target sequence. However, amplification reaction mixtures are typically assembled at room temperature, well below the temperature needed to insure primer hybridization specificity. Under such less stringent conditions, the primers may bind non-specifically to other only partially complementary nucleic acid sequences or to other primers and initiate the synthesis of undesired extension products, which can be amplified along with the target sequence. Amplification of non-specific primer extension products can compete with amplification of the desired target sequences and can significantly decrease the efficiency of the amplification of the desired sequence.

One frequently observed type of non-specific amplification product is a template-independent artifact of amplification reactions referred to as "primer dimer". Primer dimer is a double-stranded fragment whose length typically is close to the sum of the two primer lengths and appears to occur when one primer is extended over the other primer. The resulting extension product forms an undesired template which, because of its short length, is amplified efficiently.

Non-specific amplification can be reduced by reducing the formation of primer extension products prior to the start of the reaction. In one method, referred to as a "hot-start" protocol, one or more critical reagents are withheld from the reaction mixture until the temperature is raised sufficiently to provide the necessary hybridization specificity. Manual hot-start methods, in which the reaction tubes are opened after the initial high temperature incubation step and the missing reagents are added, are labor intensive and increase the risk of contamination of the reaction mixture. Alternatively, a heat sensitive material, such as wax, can be used to separate or sequester reaction components, as described in U.S. Pat. No. 5,411,876, incorporated herein by reference, and Chou et al., 1992, Nucl. Acids Res. 20(7): 1717–1723, incorporated herein by reference. In these methods, a high temperature pre-reaction incubation melts the heat sensitive material, thereby allowing the reagents to mix.

Another method of reducing the formation of primer extension products prior to the start of the reaction relies on the heat-reversible inactivation of the DNA polymerase. U.S. Pat. Nos. 5,773,258 and 5,677,152, both incorporated herein by reference, describe DNA polymerases reversibly modified by the covalent attachment of a modifier group. Incubation of the inactivated DNA polymerase at high temperature results in cleavage of the modifier-enzyme bond, thereby reactivating the enzyme.

Non-covalent reversible inhibition of a DNA polymerase by DNA polymerase-specific antibodies is described in U.S. Pat. Nos. 5,338,671, incorporated herein by reference.

Non-specific amplification also can be reduced by enzymatically degrading extension products formed prior to the start of the reaction using the methods described in U.S. Pat. No. 5,418,149, which is incorporated herein by reference. The degradation of newly-synthesized extension products is achieved by incorporating into the reaction mixture dUTP and UNG, and incubating the reaction mixture at 45–60° C. prior to carrying out the amplification reaction. Primer extension results in the formation of uracil-containing DNA, which is degraded by UNG under the pre-amplification conditions. A disadvantage of this method is that the degradation of extension product competes with the formation of extension product and the elimination of non-specific primer extension product may be less complete. An advantage of this method is that uracil-containing DNA introduced into the reaction mixture as a contamination from a previous reaction is also degraded and, thus, the method also reduces the problem of contamination of a PCR by the amplified nucleic acid from previous reactions.

Another method of reducing the formation of primer extension products prior to the start of the reaction relies on the use of primers modified at or near the 3' end by the addition of a moiety to an exocyclic amine, as described in U.S. Pat. No. 6,001,611, incorporated herein by reference.

Conventional techniques of molecular biology and nucleic acid chemistry, which are within the skill of the art, are fully explained fully in the literature. See, for example, Sambrook et al., 1989, Molecular Cloning—A Laboratory Manual, Cold Spring Harbor Laboratory, Cold Spring Harbor, N.Y.; Oligonucleotide Synthesis (M. J. Gait, ed., 1984); Nucleic Acid Hybridization (B. D. Hames and S. J. Higgins. eds., 1984); PCR Technology—principles and applications for DNA amplification, 1989, (ed. H. A. Erlich) Stockton Press, New York; PCR Protocols: A guide to methods and applications, 1990, (ed. M. A. Innis et al.) Academic Press, San Diego; and PCR Strategies, 1995, (ed. M. A. Innis et al.) Academic Press, San Diego; all of which are incorporated herein by reference.

SUMMARY OF THE INVENTION

The present invention provides methods and reagents for the in vitro amplification of a nucleic acid sequence using a primer-based amplification reaction which provide a simple and economical solution to the problem of non-specific amplification. The methods involve the use of oligonucleotide primers containing particular modifications to the sugar-phosphate backbone at or near the 3' terminus.

In one embodiment, the methods involve the use of a modified primer consisting essentially of an oligonucleotide in which at least one of the three 3' terminal nucleotides is a modified nucleotide selected from the group consisting of 2'-O-methyl-nucleotides, 2'-amino-nucleotides, and 2'-fluoro-nucleotides.

In another embodiment, the methods involve the use of a modified primer consisting essentially of an oligonucleotide in which at least one of the three 3' terminal nucleotides is a modified nucleotide that contains arabinose.

One aspect of the invention relates to kits for the in vitro amplification of a nucleic acid sequence using a primer-based amplification reaction, which kits comprise at least one modified primer, preferably two, for each intended target. A kit typically will comprise one or more amplification reagents, e.g., a nucleic acid polymerase, nucleoside triphosphates, or suitable buffers. Optionally, a kit may comprise addition components, such as a means for detecting the amplified product.

Another aspect of the present invention relates to methods for amplifying a nucleic acid which comprise carrying out a primer-based nucleic acid amplification reaction using at least one modified primer. Thus, the present invention provides a method for the amplifying a target nucleic acid contained in a sample, comprising:

(a) providing an amplification reaction mixture comprising the target nucleic acid and a pair of primers, wherein one or both members of the pair of primers are modified primers; and (b) treating the reaction mixture of step (a) under conditions suitable for the amplification of the nucleic acid.

In a preferred embodiment of the invention, the amplification reaction is a polymerase chain reaction (PCR) wherein at least one and, preferably all, of the primers are modified.

Another aspect of the invention relates to amplification reaction mixtures which contain at least one modified primer. In a preferred embodiment, the amplification reaction mixture contains a pair of modified oligonucleotide primers for carrying out a PCR.

DETAILED DESCRIPTION OF THE INVENTION

To aid in understanding the invention, several terms are defined below.

The terms "nucleic acid" and "oligonucleotide" refer to polydeoxyribonucleotides (containing 2'-deoxy-D-ribose), to polyribonucleotides (containing D-ribose), and to any other type of polynucleotide which is an N glycoside of a purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise non-purine or non-pyrimidine nucleotide analogs.

Oligonucleotides can be prepared by any suitable method, including direct chemical synthesis by a method such as the phosphotriester method of Narang et al., 1979, *Meth. Enzymol.* 68:90–99; the phosphodiester method of Brown et al., 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3):165–187, incorporated herein by reference.

The term "primer" refers to an oligonucleotide capable of acting as a point of initiation of DNA synthesis under conditions in which synthesis of a primer extension product complementary to a nucleic acid strand is induced, i.e., either in the presence of four different nucleoside triphosphates and an agent for extension (e.g., a DNA polymerase or reverse transcriptase) in an appropriate buffer and at a suitable temperature. A primer is preferably a single-stranded DNA. The appropriate length of a primer depends on the intended use of the primer but typically ranges from 10 to 50 nucleotides, preferably from 15–35 nucleotides. Short primer molecules generally require lower temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in, for example, the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning of the amplified product. The region of the primer which is sufficiently complementary to the template to hybridize is referred to herein as the hybridizing region.

As used herein, a "modified primer" refers to a primer that includes at least one nucleotide containing a sugar other than the conventional 2'-deoxy-D-ribose or D-ribose found in naturally occurring DNA and RNA. Similarly, as used herein, a "modified nucleotide" refers to a nucleotide containing a sugar other than the conventional 2'-deoxy-D-ribose or D-ribose found in naturally occurring DNA and RNA, and encompasses nucleotides in which the sugar is modified by the addition or substitution of a side group, or in which the sugar is a stereoisomer of the conventional 2'-deoxy-D-ribose or D-ribose found in naturally occurring DNA and RNA, or both. The terms are not used to indicate that a modified primer or nucleotide is the product of a process of modification, but rather to indicate the presence of differences in the oligonucleotide backbone relative to naturally occurring DNA or RNA. In particular, the primers of the present invention preferably are synthesized to contain a modified nucleotide, although the chemical modification of a primer initially containing only conventional nucleotides may provide an alternative synthesis.

The terms "target", "target sequence", "target region", and "target nucleic acid" refer to a region or subsequence of a nucleic acid which is to be amplified.

The term "hybridization" refers the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which only fully complementary nucleic acid strands will hybridize are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair concentration of the oligonucleotides, ionic strength, metal cation, and incidence of mismatched base pairs, following the guidance provided by the art (see, e.g., Sambrook et al., 1989, *Molecular Cloning—A Laboratory Manual*, Cold Spring Harbor Laboratory, Cold Spring Harbor, N.Y.; and Wetmur, 1991, Critical Review in Biochem. and Mol. Biol. 26(3/4):227–259; both incorporated herein by reference).

As used herein, a primer is "specific" for a target sequence if, when used in an amplification reaction under sufficiently stringent conditions, the primer can be extended only if hybridized to the target nucleic acid. Typically, a primer is specific for a target sequence if the primer-target duplex stability, particularly in the region of the 3' terminus of the primer, is greater than the stability of a duplex formed between the primer and any other sequence found in the sample. One of skill in the art will recognize that various factors, such as base composition of the primer and the location of the mismatches, will affect the specificity of the primer, and that routine experimental confirmation of the primer specificity will be needed in most cases. Hybridization conditions under which a target-specific primer will be extendable only if hybridized with a target sequence can be determined empirically in a routine manner. Thus, the use of target-specific primers under suitably stringent amplification conditions enables the specific amplification of those target sequences which contain the target primer binding sites. The use of sequence-specific amplification conditions enables the specific amplification of those target sequences which contain the exactly complementary primer binding sites.

The term "non-specific amplification" refers to the amplification of nucleic acid sequences other than the target sequence which results from primers hybridizing to sequences other than the target sequence and then serving as a substrate for primer extension. The hybridization of a primer to a non-target sequence is referred to as "non-specific hybridization" and can occur during the lower temperature, reduced stringency, pre-amplification conditions. One of skill in the art will understand that even highly unstable duplexes, although highly disfavored in an equilibrium state, may form transiently.

The term "primer dimer" is used herein generically to encompasses template-independent non-specific amplification product. Primer dimer is believed to result from primer extensions wherein another primer serves as a template, although the genesis of primer dimer is not well understood. The resulting amplification product typically appears to correspond approximately to a concatamer of two primers, i.e., a dimer, although concatamers of more than two primers also occur.

The term "reaction mixture" refers to a solution containing reagents necessary to carry out a given reaction. An "amplification reaction mixture", which refers to a solution containing reagents necessary to carry out an amplification reaction, typically contains oligonucleotide primers and a nucleic acid polymerase in a suitable buffer. A "PCR reaction mixture" typically contains oligonucleotide primers, a DNA polymerase (most typically a thermostable DNA polymerase), dNTP's, and a divalent metal cation in a suitable buffer. A reaction mixture is referred to as complete if it contains all reagents necessary to enable the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits of the invention may contain any subset of the reaction components which includes the modified primers of the invention.

All patents, patent applications, and publications cited herein, both supra and infra, are incorporated herein by reference.

Modified Primers

The modified amplification primers of the present invention contain particular modifications to the sugar-phosphate backbone at or near the 3' terminus. In one embodiment, the modified primers consist essentially of an oligonucleotide in which at least one of the three 3' terminal nucleotides is a modified nucleotide selected from the group consisting of 2'-O-methyl-nucleotides, 2'-amino-nucleotides, and 2'-fluoro-nucleotides. In a preferred embodiment, the modified primers consist essentially of an oligonucleotide in which at least one of the three 3' terminal nucleotides is a modified nucleotide selected from the group consisting of 2'-O-methyl-ribonucleotides, 2'-deoxy-2'-amino-nucleotides, and 2'-deoxy-2'-fluoro-nucleotides. These modifications represent the addition of a moiety to the 2' OH, or the replacement of the 2' OH by an alternative moiety.

In another embodiment, the modified primer consists essentially of an oligonucleotide in which at least one of the three 3' terminal nucleotides is a modified nucleotide that contains arabinose. Arabinose is a stereoisomer of ribose that differs only in the configuration about C-2. It is expected that embodiments in which 2'position of the arabinose is modified by the addition of a moiety to the 2' OH or replacement of the 2'-OH by an alternative moiety will be useful in the methods of the present invention. In a preferred embodiment, the modified primer consists essentially of an oligonucleotide in which at least one of the three 3' terminal nucleotides is a modified nucleotide that contains an unmodified arabinose.

The design and use of amplification primers in general is well known in the art. The primers of the present invention are distinguished by the inclusion of the specified modified nucleotides in the primer sequence. Other aspects of the primer, such as the overall length and sequence, are selected following the standard practice of primer design.

Typically, primers consist of a single strand of deoxyribonucleotides (DNA) and contain the conventional bases: the two purine bases, adenine and guanine, and the two pyrimidine bases, cytosine and thymine. However, the present invention is not limited to primers consisting only of the conventional bases. Base analogs may be used, for example, to alter the hybridization stability of the primer-target duplex. Any base analog which can be used in an unmodified amplification primer can be used in the primers of the present invention. Examples of base analogs, also referred to as unconventional bases, include 3-methyladenine, 7-methylguanine, 3-methylguanine, 5-methyl cytosine, and 5-hydroxymethyl cytosine.

Theory of Operation

A primer-based amplification involves repeated primer extensions in which the primers first hybridize to target nucleic acid and then are enzymatically extended. The specificity of the amplification depends on the specificity of the primer hybridization. One hypothesis is that non-specific amplification occurs when an unstable, transient hybridization duplex is formed between a primer and a non-target molecule, possibly another primer, in which the 3' end of the primer is momentarily paired with a complementary base in the other molecule. Initial primer extension results in the formation of complementary sequence which stabilizes the duplex and allows further extension.

While not being constrained by the theory, it is believed that the modified primers of the present invention reduce non-specific amplification by increasing the time required for the initial primer extension to occur. The backbone modifications probably delay the initial extension by rendering the primer-target duplex a less preferred template for extension. The delay in the initial extension reduces the likelihood that an unstable, transient hybridization duplex, such as between primers under pre-reaction conditions, will exist for a sufficient time to permit primer extension.

In contrast, primer-target hybridization duplexes are sufficiently stable under the primer hybridization condition used in an amplification such that the additional time required does not hinder extension. Thus, under this model, the modification does not significantly inhibit primer extension under the amplification conditions, but does decrease the probability of extension of primers involved in unstable, transient duplexes formed with non-target sequences under the pre-amplification conditions.

The 2'-O-methyl-ribonucleotides, 2'-deoxy-2'-amino-nucleotides, and 2'-deoxy-2'-fluoro-nucleotides, relative to a typical oligodeoxynucleotide primer, contain bulkier side groups bound to C-2 of the sugar. It is likely that the side group sterically interferes with the binding of the enzyme to the primer-target duplex, but not enough to preclude extension. This suggests that additional side groups of similar bulk would have a similar effect and also could be used in the methods of the invention.

The arabinose-containing nucleotides, by changing the orientation of the H and OH side groups bound to the C-2 of the sugar, alter the interaction with the enzyme. It is likely that other stereoisomers may inhibit, but not preclude, extension, and these compounds are expected to be useful in the methods of the invention.

Synthesis of Modified Primers

Synthesis of the modified primers is carried out using standard chemical means well known in the art, for example, the diethylphosphoramidite method of Beaucage et al., 1981, *Tetrahedron Lett.* 22:1859–1862; and the solid support method of U.S. Pat. No. 4,458,066, each incorporated herein by reference.

Preferably, the synthesis reaction is carried out in a commercially available automatic DNA synthesizer (e.g., ABI 374 DNA synthesizer from Applied Biosystems, Foster City, Calif.) using commercially available nucleotide phosphoramidites (e.g., from Applied Biosystems, Foster City, Calif.). Nucleotide phosphoramidites and supports suitable for synthesizing oligonucleotides containing modified nucleotides as used herein are commercially available from, for example, Glen Research (Sterling, Va.).

Standard oligonucleotide synthesis is carried out by the stepwise addition of nucleoside monomers to a growing chain. Each addition involves the coupling of a reactive 3' phosphorous group of a nucleoside monomer to the 5' hydroxyl of another nucleoside bound to a solid support. After addition of the final nucleoside, the oligonucleotide is cleaved from the support, protecting groups are removed from the bases, and the oligonucleotide is purified for use.

Using standard synthesis methods, 3' terminal nucleotide in the final oligonucleotide is derived from the nucleoside initially bound to the solid support. Thus, synthesis of oligonucleotides containing a 3' terminal modified nucleotide is carried out starting with a solid support containing the modified nucleoside. Synthesis of oligonucleotides containing an internal modified nucleotide is carried out using the appropriate nucleoside phosphoramidite monomers.

The 2'-O-methylribonuclesides are commercially available both as phosphoramidites and pre-attached to a synthesis support. Other modified nucleotides may be readily available only as phosphoramidites. Alternative synthesis supports are available that enable the synthesis of oligonucleotides with a 3' terminal modified nucleotide using the phosphoramidites of the modified nucleoside monomers. For example, universal supports, such as marketed by Glen Research (Sterling, Va.) under license from Avecia Ltd., allow cleavage of the synthesized oligonucleotide from the solid support between the first and second 3' monomers. A modified nucleoside destined to become the 3' terminal nucleoside is added in the first monomer addition and, thus, becomes the second monomer in the growing chain. Following the final addition, the 3' terminal nucleoside, originally attached to the support, is eliminated during the final cleavage step, leaving the desired terminal-modified nucleotide.

Amplifications Using Modified Primers

The methods of the present invention comprise carrying out a primer-based amplification, wherein at least one of the primers is a modified primer of the present invention. In general, the modified primers can be substituted for unmodified primers containing the same nucleotide sequence in a primer-based amplification with only routine modifications in the amplification reaction conditions following the guidance herein.

In a preferred embodiment, the modified primers of the present invention are used in the polymerase chain reaction (PCR), described in U.S. Pat. Nos. 4,683,195; 4,683,202; and 4,965,188; Saiki et al., 1985, Science 230:1350–1354; Mullis et al., 1986, Cold Springs Harbor Symp. Quant. Biol.

51:263–273; and Mullis and Faloona, 1987, Methods Enzymol. 155:335–350; each of which is incorporated herein by reference. However, the invention is not restricted to any particular amplification system. The use of the modified primers in other primer-based amplification methods in which primer dimer or non-specific amplification product can be formed is expected to be useful. Examples of primer-based amplification methods include the strand displacement assay (Walker et al., 1992, Proc. Natl. Acad. Sci. USA 89:392–396, Walker et al. 1992, Nucleic Acids Res. 20:1691–1696, and U.S. Pat. No. 5,455,166) and the transcription-based amplification methods, including the methods described in U.S. Pat. Nos. 5,437,990; 5,409,818; and 5,399,491; the transcription amplification system (TAS) (Kwoh et al., 1989, Proc. Natl. Acad. Sci. USA 86:1173–1177); and self-sustained sequence replication (3SR) (Guatelli et al., 1990, Proc. Natl. Acad. Sci. USA 87:1874–1878 and WO 92/08800). All of the above references are incorporated herein by reference. A survey of amplification systems is provided in Abramson and Myers, 1993, Current Opinion in Biotechnology 4:41–47, incorporated herein by reference.

Enzymes for use in the nucleic acid amplification methods described above are well known in the art. For example, DNA polymerases and mutants thereof useful for various applications of PCR are described in U.S. Pat. Nos. 4,889,818; U.S. Pat. No. 5,079,352; U.S. Pat. No. 5,352,600; U.S. Pat. No. 5,374,553; U.S. Pat. No. 5,405,774; U.S. Pat. No. 5,420,029; U.S. Pat. No. 5,455,170; U.S. Pat. No. 5,466,591; U.S. Pat. No. 5,491,086; U.S. Pat. No. 5,618,711; U.S. Pat. No. 5,624,833; U.S. Pat. No. 5,674,738; U.S. Pat. No. 5,677,152; U.S. Pat. No. 5,773,258; U.S. Pat. No. 5,789,224; U.S. Pat. No. 5,795,762; U.S. Pat. No. 5,939,292; U.S. Pat. No. 5,968,799; European patent publication No. 892,058; European patent publication No. 823,479; European Patent Publication No. 0 902,035; and co-pending U.S. application Ser. No. 09/146,631, each incorporated herein by reference. Additional enzymes for use in other nucleic acid amplification methods also are well known in the art and described in, for example, the references cited above which describe the amplification methods.

One of skill in the art will understand that the magnitude of the effect of the modified primers will depend on the particular amplification reaction and reaction conditions selected. The magnitude of the effect can be determined empirically, following the teaching in the examples.

DNA polymerases require a divalent cation for catalytic activity. For extension reactions using a thermoactive or thermostable DNA polymerase and a DNA template, the preferred divalent cation is $Mg^{+2}$, although other cations, such as $Mn^{+2}$ or $Co^{+2}$ can activate DNA polymerases. The use of $Mn^{+2}$ to increase the efficiency of extension reactions using an RNA template, i.e., reverse-transcription, is described in U.S. Pat. No. 5,310,652; U.S. Pat. No. 5,322,770; U.S. Pat. No. 5,407,800; U.S. Pat. No. 5,561,058; U.S. Pat. No. 5,641,864; and U.S. Pat. No. 5,693,517; all incorporated herein by reference. The use of $Mn^{+2}$ also decreases the fidelity of amplifications, either using an RNA or a DNA template. In general, the use of $Mn^{+2}$ decreases the delay of the template amplification resulting from the use of the modified primers when compared to an amplification carried out using $Mg^{+2}$.

Particular mutant DNA polymerases may be useful in the present invention. Co-pending U.S. application Ser. No. 60/198,336, incorporated herein by reference, describes the use of particular mutant DNA polymerases, which are described in European Patent Publication No. 0 902,035 and co-pending U.S. application Ser. No. 09/146,631, both incorporated herein by reference, to achieve more efficient high-temperature reverse-transcription and RNA amplification reactions, particularly in $Mg^{+2}$-activated reactions. As described in the examples, this particular mutation tends to decrease the delaying effect of the modified primers on target amplification when used in the methods of the present invention. DNA polymerases derived from *Thermatoga maritima*, described in patents cited above, may provide similar advantages when used in the present methods.

The selection of suitable primer modifications, enzymes, cation, and other reaction reagents and conditions will depend on the application. In some application, the minimization of primer dimer may be more important than the target amplification efficiency. In other applications, it may be desirable to maintain target amplification efficiency as much as possible while decreasing primer dimer. One of skill will understand that suitable reaction conditions in general, and the enzyme and divalent cation in particular, can be selected empirically for any particular application using routine experimental methods, following the guidance herein and in the examples.

The present invention is compatible with other methods of reducing non-specific amplification, such as those described in the references cited supra. For example, the present invention can be used in an amplification carried out using a reversibly inactivated enzyme as described in U.S. Pat. Nos. 5,677,152, and 5,773,258, each incorporated herein by reference. The use of a reversibly inactivated enzyme, which is re-activated under the high temperature reaction conditions, further reduces non-specific amplification by inhibiting primer extension of any modified primers prior to the start of the reaction. A reversibly inactivated thermostable DNA polymerase, developed and manufactured by Hoffman-La Roche (Nutley, N.J.) and marketed by Applied Biosystems (Foster City, Calif.), is described in Birch et al., 1996, Nature 381(6581):445–446, incorporated herein by reference.

The present invention also can be used in conjunction with the modified primers described in U.S. Pat. No. 6,001,611, incorporated herein by reference. As described therein, primers can be modified by the covalent attachment of a modifier group to the exocyclic amine of a nucleotide at or near the 3' terminus. The attachment of a group to the exocyclic amine does not interfere with the use of modified nucleotides at or near the 3' terminus, as specified herein. Suitable combinations of primer modifications for use with a particular target and reaction conditions can be selected by routine experimentation as described in the examples, below.

Sample preparation methods suitable for amplification reactions are well known in the art and fully described in the literature cited herein. The particular method used is not a critical part of the present invention. One of skill in the art can optimize reaction conditions for use with the known sample preparation methods.

Methods of analyzing amplified nucleic acid are well known in the art and fully described in the literature cited herein. The particular method used is not a critical part of the present invention. One of skill in the art can select a suitable analysis method depending on the application.

A preferred method for analyzing an amplification reaction is by monitoring the increase in the total amount of double-stranded DNA in the reaction mixture, as described in Higuchi et al., 1992, Bio/Technology 10:413–417; Higuchi et al., 1993, Bio/Technology 11:1026–1030; Higuchi and Watson, 1999, in PCR Applications (Innis et al., eds.)

Chapter 16, Academic Press, San Diego; U.S. Pat. No. 5,994,056; and European Patent Publication Nos. 487,218 and 512,334, each incorporated herein by reference. In this method, referred to herein as "kinetic PCR", the detection of double-stranded DNA relies on the increased fluorescence that ethidium bromide (EtBr) and other DNA binding labels exhibit when bound to double-stranded DNA. The amplification is carried out in the presence of the label. The increase of double-stranded DNA resulting from the synthesis of target sequences results in an increase in the amount of label bound to double-stranded DNA and a concomitant detectable increase in fluorescence, which is monitored during the amplification. Thus, the methods enable monitoring the progress of an amplification reaction.

In a kinetic PCR, the measured fluorescence depends on the total amount of double-stranded DNA present, whether resulting from non-specific amplification or from amplification of the target sequence. Monitoring the fluorescence allows measurement of the increase in the total amount of double-stranded DNA is measured, but the increase resulting from amplification of the target sequence is not measured independently from the increase resulting from non-specific amplification product. The modified primers of the present invention are particularly useful in kinetic PCR because they not only reduce the amount of primer dimer formed, but also delay the formation of detectable amounts of primer dimer. A delay of primer dimer formation until after a significant increase in target sequence has occurred enables independent monitoring of the amplification of target sequences and minimizes the interference from primer dimer.

Kits

The present invention also relates to kits, typically multi-container units comprising useful components for practicing the present method. A useful kit contains primers, at least one of which is modified as described herein, for nucleic acid amplification. Other optional components of the kit include, for example, an agent to catalyze the synthesis of primer extension products, the substrate nucleoside triphosphates, appropriate reaction buffers, and instructions for carrying out the present method.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLE 1

Protocols Used for Testing the Modified Primers

The effects of various modified primers on the formation of primer dimer were tested by comparing amplifications carried out using modified or unmodified primers. The comparisons were carried out using a protocol essentially as described below. Where the protocol was modified, the changes are indicated in the description of the experiment.

Target Nucleic Acid

Plasmids containing a segment of HIV-1 subtype O DNA from the gag gene were used as a target.

Primers

Amplifications were carried out using both modified and unmodified primers. The nucleotide sequences of the primers are shown below, oriented in the 5' to 3' direction. These primers amplify a portion of the gag gene from an HIV-1 sequence.

The three upstream primers are variants of the same primer, each fully complementary to the target sequence, but differing in the terminal nucleotide (A, T, or G). This allows comparisons of the effects of modification of terminal nucleotides while minimizing the effects of primer sequence differences.

| Amplification Primer Sequences | |
|---|---|
| Upstream | |
| SK145-T AGTGGGGGGACATCAAGCAGCCATGCAAA | (SEQ ID NO: 1) |
| SK145 AGTGGGGGGACATCAAGCAGCCATGCAAAT | (SEQ ID NO: 2) |
| SK145+G AGTGGGGGGACATCAAGCAGCCATGCAAATG | (SEQ ID NO: 3) |
| Downstream | |
| GAG152 GGTACTAGTAGTTCCTGCTATGTCACTTCC | (SEQ ID NO: 4) |

The modified primers consist of the same nucleotide sequences but with one of more of the 3' terminal nucleotides being a modified nucleotide. The following abbreviations are used to identify the nucleotides.

| Nucleotide | Abbreviation |
|---|---|
| unmodified nucletoides | dA, dT, dG, dC |
| 2'-O-methyl-ribonucleotides | 2'omeA, 2'omeU, 2'omeG, 2'omeC |
| 2'-deoxy-2'-amino-nucleotides | $2'NH_2A$, $2'NH_2U$, $2'NH_2G$, $2'NH_2C$ |
| 2'-deoxy-2'-fluoro-nucleotides | 2'FA, 2'FU, 2'FG, 2'FC |
| arabinose-containing nucleotides | AraA, AraU, AraG, AraC |

As each of the above primers differs in the 3' terminal nucleotide, primers are identified by the terminal nucleotide in the examples, below. For primers containing additional upstream modified nucleotides, the terminal two or three nucleotides are shown, as needed. Thus, for example, an upstream primer identified as 2'omeG refers to a primer having sequence SK145+G (SEQ ID NO: 3), wherein the 3' terminal nucleotide is a 2'-O-methyl-guanosine. Analogously, a upstream primer identified as 2'omeA-dA refers to a primer having sequence SK145-T (SEQ ID NO: 1), wherein the 3' penultimate nucleotide is a 2'-O-methyl-adenosine and the 3' terminal nucleotide is an unmodified adenosine.

Primers were synthesized on an ABI 394 DNA synthesizer (Perkin Elmer, Applied Biosystems Division, Foster City, Calif.). The modified nucleoside phosphoramidites were obtained for example Glen Research (Sterling, Va.). Conventional synthesis conditions were used, essentially as recommended by the manufacturers.

The crude primers were purified by standard DMT On/Off HPLC using a Rainin Pure-DNA column on a Rainin HPLC system (Rainin Instrument Go, Woburn, Mass.). The oilgonucleotides were analyzed using a capillary electrophoresis system (Applied Biosystems, Foster City, Calif.) or by denaturing anion-exchange HPLC chromatography on a Nucleopak column (Dionex Corp. Sunnyvale, Calif.).

DNA polymerases

Amplifications were carried out using the thermostable DNA polymerase from Thermus species ZO5 described in U.S. Pat. No. 5,455,170, and U.S. Pat. No. 5,674,738, incorporated herein by reference.

Amplifications also were carried out using two mutant forms of a DNA polymerase from *Thermus thermophilus* (Tth). Tth is described in U.S. Pat. No. 5,618,711, incorporated herein by reference.

One of the mutant Tth DNA polymerases, designated herein CE31, contains point mutations Q682K and E683K, where the number indicates the amino acid position of the mutation, the prefix letter is the standard singe-letter code for the amino acid in the native enzyme, and the suffix letter is the standard singe-letter code for the amino acid in the mutant enzyme. The E683K mutation increases the DNA polymerase's ability to incorporate nucleotides, including deoxynucleotides (dNTP's) and nucleotide analogs such as dideoxynucleotides (ddNTP's), labeled with fluorescein and cyanine family dyes, as descibed in European Patent Publication No. 0 902,035 and co-pending U.S. application Ser. No. 09/146,631, both incorporated herein by reference. Co-pending U.S. application Ser. No. 60/198,336, incorporated herein by reference, describes the use of these mutant DNA polymerases to provide more efficient high-temperature reverse-transcription and RNA amplification reactions, particularly in $Mg^{+2}$-activated reactions.

The other mutant Tth DNA polymerase, designated herein CE18, contains point mutations Q682K and E683K and G46E. The G46E mutation essentially eliminates 5' to 3' exonuclease activity, as described in U.S. Pat. No. 5,466,591, incorporated herein by reference. CE18 differs from CE31 only by the presence of the G46E mutation. It is expected that the presence or absence of this point mutation in the enzyme's 5' to 3' exonuclease domain has no affect on the ability of the enzyme to extend a modified primer.

Amplification Conditions

Amplifications were carried out in 100 µl reactions volumes containing the following reagents, except where noted:

Either no target (negative controls) or $10^4$–$10^6$ copies of HIV template DNA 0.5 µM of each primer (50 pmoles)

5–50 units of DNA polymerase 50 mM Tricine (pH 8.3)

120 mM KOAc

300 µM each dATP, dCTP, and dGTP

600 µM dUTP 3 mM MnOAc 8.5% Glycerol 10 units of UNG*

1.0 µg/ml ethidium bromide.

* manufactured and developed by Hoffman-La Roche and marketed by Applied Biosystems (Foster City, Calif.).

Thermal cycling of each reaction was carried out in a GeneAmp® PCR system 9600 thermal cycler (Applied Biosystems, Foster City, Calif.) modified to facilitate monitoring of the fluorescence of the ethidium bromide during the reaction, as described in Higuchi and Watson, 1999, in PCR Applications (Inis et al., eds.) Chapter 16, Academic Press, San Diego, incorporated herein by reference. Alternatively, reactions can be carried out in a ABI PRISM® 7700 Sequence Detection System (Applied Biosystems, Foster City, Calif.), which allows the selection of detection wavelengths for use with different dyes, or in a GeneAmp® 5700 Sequence Detection System (Applied Biosystems, Foster City, Calif.), which is designed with a preset detection wavelength to be used with SYBR® Green I (Molecular Probes, Eugene, Oreg.). The thermal cycling was carried out using the following temperature profile, except where noted:

| | |
|---|---|
| Pre-reaction incubation | 48° C. for 12 minutes |
| High-Temp incubation | 96° C. for 10 seconds |
| up to 60 cycles: | denature at 91° C. for 10 seconds, |
| | anneal/extend at 65° C. for 40 seconds. |

The pre-reaction incubation is to allow the UNG to facilitate the degradation of any dU-containing primer extension products formed during the low temperature reaction setup, as described in U.S. Pat. No. 5,418,149, incorporated herein by reference. Temperature cycling was carried out for 60 cycles in most reactions, although some reactions were stopped at an earlier cycle.

Detection of Amplified Product

The accumulation of amplified product was measured at each cycle during the reaction using the kinetic PCR methods described above. The fluorescence of the ethidium bromide in the reaction mixture, which fluoresces more strongly when intercalated into double-stranded DNA, was monitored to measure the increase in double-stranded DNA during amplification. Reactions were monitored by measuring the fluorescence of the reaction mixture in each cycle.

Fluorescence measurements were normalized by dividing by an initial fluorescence measurement obtained during a cycle early in the reaction while the fluorescence measurements between cycles were relatively constant, i.e., prior to a detectable increase in reaction product. The cycle number chosen for the initial fluorescence measurement was the same for all reactions compared, so that all measurements represent increases relative to the same reaction cycle.

The increase in reaction product during the reaction was measured as the number of amplification cycles carried out until the normalized fluorescence exceeded an arbitrary fluorescence level (AFL). The AFL was chosen close to the baseline fluorescence level, but above the range of random fluctuations in the measured fluorescence, so that the reaction kinetics were measured during the geometric growth phase of the amplification. In later cycles, accumulation of amplified product inhibits the reaction and eventually leads to a reaction plateau.

An AFL of 1.2 was chosen for all reactions. Because a PCR amplification consists of discrete cycles and the fluorescence measurements are carried out once per cycle, the measured fluorescence typically increases from below the AFL to above the AFL in a single cycle. To improve the precision of the measurements, an "exact" number of cycles to reach the AFL threshold, referred to herein as the $C_T$ value, was calculated by interpolating fluorescence measurements between cycles.

Because the kinetic PCR methods only measure an increase in the total amount of double-stranded DNA, non-specific amplification product is not measured independently of the intended amplification product. To measure the production of template-independent, non-specific amplification products (primer dimer), separate reactions were carried out without template nucleic acid in the reaction mixture. In such template-free reactions, any increase in double-stranded DNA is attributable to the formation of template-independent non-specific amplification product, i.e. "primer dimer."

In most reactions, if enough amplification cycles are carried out, primer dimer eventually is formed and, once formed, primer dimer is amplified efficiently because of its small size. However, the generation of primer dimer does not affect the $C_T$ observed from the target amplification as long as primer dimer is not detectable until well after the $C_T$ of the target amplification. Preferably, the formation of primer dimer is delayed so that it is not formed within the number of cycles used in the reaction.

Even a minor delay in the formation of primer dimer relative to the target amplification can provide significant benefits in a reaction. Because of the rapid accumulation of amplified product during the geometric growth phase of a PCR—each cycle results in almost a doubling of the quantity of amplified product—each cycle of delay in the formation of primer dimer relative to target amplification nearly halves the amount of primer dimer present relative to the amount of target. This reduction in the relative amount of primer dimer helps to minimize any effects of primer dimer formation on the target $C_T$.

The modified primers typically have some effect, usually a delay, on the formation of the desired amplification product. Preferably, this delay is minimized while the delay in the formation of primer dimer is maximized. Because the absolute $C_T$ obtained in an amplification of target depends on the initial target concentration, the results from the reactions containing the target template were analyzed by comparing the difference in the $C_T$ values obtained, designated $\Delta C_T$, between reactions using modified primers and comparable reactions using unmodified primers. Thus, preferred modified primers are those which provide a minimal change in $C_T$ of the target amplification and provide a maximal increase in $C_T$ of the no-target amplifications.

EXAMPLE 2

Results Using Unmodified Primers

To provide a measure of the formation of primer dimer which can be used to evaluate the improvements obtained using the modified primers, amplifications were carried out without target template using unmodified versions of primers SK145 (SEQ ID NO: 2) and GAG152 (SEQ ID NO: 4). The reactions were carried out over a range of DNA polymerase concentrations. Representative $C_T$ values observed from the template-free reactions are shown in the table, below.

| Template-free Reactions | |
|---|---|
| Enzyme | $C_T$ |
| 10 U Z05 | 38.0 |
| 20 U Z05 | 37.0 |
| 1.25 U CE31 | 37.1 |
| 2.5 U CE31 | 35.9 |
| 5 U CE31 | 35.5 |
| 10 U CE31 | 33.9 |
| 20 U CE31 | 31.4 |

For both DNA polymerases, primer dimer tends to be formed earlier at higher enzyme concentrations. In general, reactions using CE31 DNA polymerase resulted in primer dimer earlier (lower $C_T$ value) than those using Z05 DNA polymerase.

Amplifications were carried out (data not shown) comparing primer dimer formation in reactions using unmodified forms of the three upstream primers. Nearly identical results were obtained using the three upstream primers. For this reason, in the comparisons of modified primers to unmodified primers described below, the three possible unmodified primer pairs were used interchangeably.

It should be noted that $C_T$ values from template-free reactions tends to be more variable than $C_T$ values from amplifications of template. This probably reflects the randomness in the time to form the initial primer dimer template, which may not occur in some reactions. Once formed, primer dimer is amplified efficiently because of its small size. As shown below, although primer dimer usually became detectable in replicate reactions at about the same cycle number, in some reactions primer dimer was significantly delayed or did not form at all in one of the replicates.

EXAMPLE 3

Results using 2'-O-methyl Modified Primers

The results of amplification using a variety of modified primer combinations are reported in the tables, below. The primer modifications, the enzyme, and the enzyme concentration used in each reaction are indicated in the table.

The results from the amplifications of target template, which yield the intended amplification product ("amplicon"), are reported as the difference in $C_T$ ($\Delta C_T$) between reactions carried out with the indicated modified primers and reactions using unmodified primers. Amplifications typically were carried out in duplicate and the averaged results are reported in the table, below.

The results from the amplifications using template-free reactions, which yield only primer dimer, if anything, are reported as the $C_T$. In most cases, the results reported are the average of duplicate reactions. In duplicate reactions in which primer dimer became detectable at significantly different cycle numbers, i.e., in which the $C_T$ values were quite different (for example, wherein primer dimer was not formed in one replicate), both values are reported separately. In reactions in which no primer dimer was detected by the final cycle in which fluorescence measurements were made, the final reaction cycle number is reported and result is flagged with an asterisk.

I. 3'-terminal 2'-O—Me Modified Primers

The results of amplifications carried out using primers that contain a modified nucleotide at the 3' terminal position are shown in the tables, below.

| Amplifications using ZO5 DNA polymerase | | | | |
|---|---|---|---|---|
| Primers | | | Amplicon | primer dimer |
| Upstream | Downstream | Enzyme | $\Delta C_T$ | $C_T$ |
| 2'omeG | dC | 50 U Z05 | 0.9 | 45.0 |
| | | 25 U Z05 | 1.0 | 42.0 |
| | | 12.5 U Z05 | 1.0 | 42.5 |
| 2'omeG | 2'omeC | 50 U Z05 | 1.0 | 49.3–*59 |
| | | 25 U Z05 | 1.0 | 45.4–*59 |
| | | 12.5 U Z05 | 1.1 | *59 |
| 2'omeU | dC | 50 U Z05 | 1.2 | 43.2 |
| | | 25 U Z05 | 0.5 | 41.6 |
| | | 12.5 U Z05 | 1.0 | 43.0 |
| 2'omeU | 2'omeC | 50 U Z05 | 1.8 | 46.5 |
| | | 25 U Z05 | 1.4 | 45.0 |
| | | 12.5 U Z05 | 1.5 | 46.6–*53 |
| 2'omeA | dC | 50 U Z05 | 5.0 | 44.4 |
| | | 25 U Z05 | 4.5 | 46.4 |
| | | 12.5 U Z05 | 4.5 | 47.0–*50 |

The primer dimer $C_T$ values obtained can be compared to those obtained in the reactions using unmodified primers, in which $C_T$ values of 37–38 were observed. The data demonstrate that, in general, the use of at least one primer that incorporates a 3'terminal 2'-O'—Me nucleotide delays the formation of primer dimer in template-free reactions. In particular, in almost all reactions, a $C_T$ value greater than 40, usually significantly greater, was obtained.

The observed effect of a 3'-terminal 2'-O—Me ribonucleotide on the amplification of target depended on the particular base of the modified nucleotide. The use of a 3' terminal 2'-O—Me—C or U or G resulted in minimal delay of the target amplification, ranging from 0.5 cycle delay using a single modified primer to a 1.8 cycle delay using two modified primers. In contrast, in reactions using ZO5 DNA polymerase, the use of a 3' terminal 2'-O—Me—A resulted in a delay of 4–5 cycles.

| Amplifications using CE31 DNA polymerase | | | | |
|---|---|---|---|---|
| Primers | | | Amplicon | primer dimer |
| Upstream | Downstream | Enzyme | $\Delta C_T$ | $C_T$ |
| 2'omeG | 2'omeC | 20 U CE31 | 0.9 | 41.2 |
| | | 10 U CE31 | 0.8 | 43.0 |
| | | 5 U CE31 | 1.0 | 43.2 |
| 2'omeG | dC | 20 U CE31 | 0.7 | 37.0 |
| | | 10 U CE31 | 0.8 | 38.4 |
| | | 5 U CE31 | 0.7 | 39.0 |
| 2'omeU | 2'omeC | 20 U CE31 | 0.7 | 39.0 |
| | | 10 U CE31 | 0.7 | 41.2 |
| | | 5 U CE31 | 1.0 | 41.9 |
| 2'omeU | dC | 20 U CE31 | 0.3 | 36.3 |
| | | 10 U CE31 | 0.1 | 37.2 |
| | | 5 U CE31 | 0.6 | 36.2 |
| 2'omeA | 2'omeC | 20 U CE31 | 1.0 | 41.1 |
| | | 10 U CE31 | 1.0 | 42.6 |
| | | 5 U CE31 | 1.2 | 43.9 |
| 2'omeA | dC | 20 U CE31 | 1.3 | 37.0 |
| | | 10 U CE31 | 1.3 | 38.9 |
| | | 5 U CE31 | 1.9 | 40.6 |

As noted above, reactions using unmodified primers with CE31 tend to produce primer dimer at an earlier cycle than reactions using ZO5 DNA polymerase. The results obtained using 3'-terminal modified primers shows similar improvements as those observed in the reactions using ZO5 DNA polymerase. In general, amplifications of templates using CE31 tended to be less affected by the use of the 3' modified primers. In particular, the use of CE31 minimizes the delay in target amplifications carried out using a primer with a 3' terminal 2'-O—Me—A.

The results demonstrate that modified primers that contain a modified nucleotide at the 3' terminal nucleotide are useful in the present methods.

II. 3'-penultimate Nucleotide Modifications

The results from amplifications carried out using primers that contain a modified nucleotide at the 3' penultimate position are shown in the tables, below.

| Amplifications using ZO5 DNA polymerase | | | | |
|---|---|---|---|---|
| Primers | | | Amplicon | primer dimer |
| Upstream | Downstream | Enzyme | $\Delta C_T$ | $C_T$ |
| 2'omeA-dA | 2'omeC | 50 U Z05 | 3.4 | 46.5–*59 |
| | | 25 U Z05 | 2.6 | 48.3–*59 |
| | | 12.5 U Z05 | 3.2 | 49.0 |
| 2'omeA-dA | 2'omeC-dC | 50 U Z05 | 2.8 | 51.0–*59 |
| | | 25 U Z05 | 2.2 | 51.7 |
| | | 12.5 U Z05 | 2.5 | 47.0–*59 |

| Amplifications using CE31 DNA polymerase | | | | |
|---|---|---|---|---|
| Primers | | | Amplicon | primer dimer |
| Upstream | Downstream | Enzyme | $\Delta C_T$ | $C_T$ |
| 2'omeA-dA | 2'omeC | 20 U CE31 | 1.0 | 40.9 |
| | | 10 U CE31 | 0.9 | 43.5 |
| | | 5 U CE31 | 1.0 | 44.5 |
| 2'omeA | 2'omeC-dC | 20 U CE31 | 1.0 | 37.0 |
| | | 10 U CE31 | 1.5 | 38.9 |
| | | 5 U CE31 | 1.8 | 53.5 |

The results demonstrate that modified primers that contain a modified nucleotide at the 3' penultimate nucleotide are useful in the present methods.

III. 3'-terminal Two Nucleotide Modifications

The results from amplifications carried out using primers that contain two modified nucleotides, one at the 3' terminal and one at the 3' penultimate position, are shown in the tables, below.

| Amplifications using ZO5 DNA polymerase | | | | |
|---|---|---|---|---|
| Primers | | | Amplicon | primer dimer |
| Upstream | Downstream | Enzyme | $\Delta C_T$ | $C_T$ |
| 2'omeG | 2'omeC—2'omeC | 50 U Z05 | 1.6 | *59 |
| | | 25 U Z05 | 1.9 | *59 |
| | | 12.5 U Z05 | 1.8 | *59 |
| 2'omeU | 2'omeC—2'omeC | 50 U Z05 | 1.1 | 45.0–*57 |
| | | 25 U Z05 | 1.2 | 45.8–*57 |
| | | 12.5 U Z05 | 1.1 | 49.8–*57 |

| Amplifications using CE31 DNA polymerase | | | | |
|---|---|---|---|---|
| Primers | | | Amplicon | primer dimer |
| Upstream | Downstream | Enzyme | $\Delta C_T$ | $C_T$ |
| 2'omeG | 2'omeC—2'omeC | 20 U CE31 | 1.1 | 45.0–*59 |
| | | 10 U CE31 | 1.0 | 57–*59 |
| | | 5 U CE31 | 1.0 | *59 |
| 2'omeU | 2'omeC—2'omeC | 20 U CE31 | 0.8 | 40.0 |
| | | 10 U CE31 | 0.8 | 42.3–48.5 |
| | | 5 U CE31 | 1.1 | 43.5 |
| 2'omeA | 2'omeC—2'omeC | 20 U CE31 | 1.4 | 50.0 |
| | | 10 U CE31 | 1.3 | *59 |
| | | 5 U CE31 | 1.5 | *59 |

The results demonstrate that modified primers that contain modified nucleotides at the 3' terminal two positions are useful in the present methods.

Additional amplifications (data not shown) indicated that both primers may be modified at the final two 3' terminal positions. This combination is less preferred because, although primer dimer was effectively delayed, the delay in the amplification of target also was greater (approximately 3 cycles). However, under some reaction conditions, particularly wherein the maximum delay of the formation of primer dimer is paramount, the use of a pair of primers, each containing modified nucleotides at the 3' terminal two positions, would be useful.

EXAMPLE 4

Fluoro, Amino, and Arabinose-modified Primers

The results of amplification carried out using primers modified with a 2'-fluoro or 2'-amino group, or containing an arabinose nucleotide are shown in the tables, below. The amplifications were carried out essentially as described in Example 1, but using the reaction temperature profile shown below:

| | |
|---|---|
| Pre-reaction incubation | 48° C. for 12 minutes |
| High-Temp incubation | 93° C. for 2 minutes |
| up to 60 cycles: | denature at 93° C. for 10 seconds, anneal/extend at 60° C. for 40 seconds. |

In template-free amplifications using unmodified primers and 40 U Z05 DNA polymerase, a $C_T$ from primer dimer formation of 34.1 was observed. In general, the use of a lower anneal/extend temperature (60° C.) in the temperature cycling profile tends to increase the formation of primer dimer. For this reason, the $C_T$ values presented below are not directly comparable to those reported in the previous example.

The results are shown in the table, below.

Amplifications using other Primer Modifications

| Primers | | | Amplicon | primer dimer |
|---|---|---|---|---|
| Upstream | Downstream | Enzyme | $\Delta C_T$ | $C_T$ |
| dT | dC | 40 U Z05 | — | 34.1 |
| 2'NH$_2$U-dG | dC | 40 U Z05 | 0.0 | 36.9 |
| 2'FU-dG | dC | 40 U Z05 | 0.0 | 32.1 |
| dT | 2'NH$_2$C-dC | 40 U Z05 | 0.0 | 36.6 |
| dT | 2'araC-dC | 40 U Z05 | 0.0 | 37.0 |
| 2'FU-dG | 2'NH$_2$C-dC | 40 U Z05 | 1.1 | 41.5 |
| 2'NH$_2$U-dG | 2'NH$_2$C-dC | 40 U Z05 | 0.8 | 45.0 |
| 2'NH$_2$U-dG | 2'araC-dC | 40 U Z05 | 1.7 | 43.1 |

The results demonstrate that 2'-fluoro, 2'-amino, and arabinose nucleotides also provide improved results when used in modified primers in the present methods.

The results obtained using a primer containing a 2'-fluoro nucleotide when paired with another modified primer demonstrated significant improvements, even over that attributable to the second modified primer. However, the results obtained using a primer containing a 2'-fluoro nucleotide paired with an unmodified primer showed, if anything, a minor detrimental effect. The reason for this anomalous result is not apparent.

EXAMPLE 5

Primers Comparisons: $Mg^{+2}$-activated Reactions

Additional reactions were carried out essentially as described in Example 1, above, but using 3.0 mM $Mg^{+2}$ in the reaction mixture, instead of $Mn^{+2}$, and 40 units of Z05 or CE18 DNA polymerase, and the following reaction temperature profile:

| | |
|---|---|
| Pre-reaction incubation | 48° C. for 12 minutes |
| High-Temp incubation | 94° C. for 10 seconds |
| up to 60 cycles: | denature at 91° C. for 10 seconds, anneal/extend at 60° C. for 40 seconds. |

In template-free amplifications using unmodified primers and 40 U Z05 DNA polymerase, a $C_T$ from primer dimer formation of 35.1 was observed. As noted above, the use of a lower anneal/extend temperature (60° C.) in the temperature cycling profile tends to increase the formation of primer dimer. For this reason, the $C_T$ values presented below are not directly comparable to those reported in the previous example.

The results are shown in the tables, below. A "neg" in the results columns indicates that no amplification product was observed.

Amplifications using Z05 DNA polymerase

| Primers | | | Amplicon | primer dimer |
|---|---|---|---|---|
| Upstream | Downstream | Enzyme | $\Delta C_T$ | $C_T$ |
| 2'omeA | dC | 40 U Z05 | 25.3 | 55.0 |
| 2'omeA | 2'omeC | 40 U Z05 | neg | neg |
| 2'omeA-dA | dC | 40 U Z05 | 4.9 | 47.0 |
| 2'omeG | dC | 40 U Z05 | 18.9 | 49.0 |
| 2'omeU | dC | 40 U Z05 | 1.7 | 49.5 |
| dA | 2'omeC | 40 U Z05 | 0.5 | 49.0 |

Amplifications using CE18 DNA polymerase

| Primers | | | Amplicon | primer dimer |
|---|---|---|---|---|
| Upstream | Downstream | Enzyme | $\Delta C_T$ | $C_T$ |
| 2'omeA | dC | 40 U CE18 | 2.1 | 38.0 |
| 2'omeA | 2'omeC | 40 U CE18 | 21.0 | *53 |
| 2'omeG | dC | 40 U CE18 | 3.0 | 42.0 |
| 2'omeG | 2'omeC | 40 U CE18 | 3.0 | *53 |
| 2'omeU | dC | 40 U CE18 | 2.1 | 37.2 |
| 2'omeU | 2'omeC | 40 U CE18 | 1.8 | *53 |
| dA | 2'omeC | 40 U CE18 | 0.5 | 38.6 |

The results demonstrate that primers that contain modified nucleotide at the 3' terminal position can be useful in the present methods even in $Mg^{+2}$-activated amplifications, although the modified nucleotide has a greater impact on the target amplification in a $Mg^{+2}$ buffer than in a $Mn^{+2}$ buffer. In particular, a 2'-O-methyl-A at the 3' terminus of the primer significantly delays the amplification of target under these reaction conditions.

EXAMPLE 6

Multiply Modified Primers

Amplifications were carried out using upstream primer SK145 (SEQ ID NO: 2) modified by the inclusion of a 2'-O—Me ribonucleotide at every fifth position starting with the 3' terminal nucleotide. These primers are designated "⅕ome" in the tables, below. The amplifications were carried essentially as described in Example 1. The results are presented in the tables, below.

Amplifications using ZO5 DNA polymerase

| Primers | | | Amplicon | primer dimer |
|---|---|---|---|---|
| Upstream | Downstream | Enzyme | $\Delta C_T$ | $C_T$ |
| 1/5ome | dC | 50 U ZO5 | 4.5 | 56.0 |
| | | 25 U ZO5 | 4.9 | *58 |
| | | 12.5 U ZO5 | 6.3 | *58 |
| 1/5ome | 2'omeC | 20 U ZO5 | 5.9 | *51 |
| | | 10 U ZO5 | 6.9 | *51 |
| 1/5ome | 2'omeC-dC | 50 U ZO5 | 4.8 | *59 |
| | | 25 U ZO5 | 5.2 | *59 |
| | | 12.5 U ZO5 | 6.6 | *59 |

Amplifications using CE31 DNA polymerase

| Primers | | | Amplicon | primer dimer |
|---|---|---|---|---|
| Upstream | Downstream | Enzyme | $\Delta C_T$ | $C_T$ |
| 1/5ome | dC | 25 U CE31 | 1.9 | 47.0 |
| | | 12.5 U CE31 | 2.0 | 46.0 |
| | | 6.25 U CE31 | 2.0 | 46.0 |
| 1/5ome | 2'omeC | 50 U CE31 | 1.5 | *52 |
| | | 25 U CE31 | 1.5 | *42 |
| | | 20 U CE31 | 1.8 | *57 |
| | | 20 U CE31 | 1.6 | 51.0 |
| | | 5 U CE31 | 2.9 | *57 |
| | | 2.5 U CE31 | 3.9 | *45 |
| 1/5ome | 2'omeC-dC | 20 U CE31 | 2.0 | 54.0 |
| | | 10 U CE31 | 2.5 | *59 |
| | | 5 U CE31 | 3.0 | *59 |

The results demonstrate that primers that contain a modified nucleotide at every fifth nucleotide, starting with the 3' terminal nucleotide, are useful in the present methods. It is expected that the particular pattern of modification used herein is not critical, and that additional multiply modified primers will be useful in the present methods. Certainly primers that contain a modified nucleotide at every fifth nucleotide, starting with the 3' penultimate nucleotide present methods.

EXAMPLE 7

Primer Modified at the Three 3' Terminal Nucleotides

This example describes the use of a primer containing 2'-O—Me ribonucleotides at the three 3' terminal positions. These particular reactions were carried out using primers that amplify a sequence from the human parvovirus (B19) genome.

Reactions were carried out either using a pair of unmodified primers or a pair of primers in which the upstream primer, which in unmodified form terminated in A-G-T at the 3' end, terminated in 2'omeA-2'omeG-2'omeU; the downstream primer was unmodified. The reaction conditions ($Mn^{+2}$-activated reactions using ZO5 DNA polymerase) were similar to those described above for the amplification of an HIV-1 sequence, but using 20 pmoles of each parvovirus primer and a target template consisting of purified parvovirus nucleic acid. The thermal cycling was carried out using the following temperature profile:

| Pre-reaction incubation | 48° C. for 12 minutes |
|---|---|
| High-Temp incubation | 94° C. for 10 seconds |
| up to 60 cycles: | denature at 92° C. for 10 seconds, |
| | anneal/extend at 62° C. for 60 seconds. |

The results of the amplifications are presented in the table, below. As the propensity to form primer dimer is known to be system-dependent, the present results are not directly comparable to those presented in the previous examples. However, despite the differences in reactions, the $C_T$ observed in the template-free amplifications using unmodified parvovirus primers (37.0) are comparable to those observed using the unmodified HIV primers in the reactions described in Example 2.

Amplifications using a Triply-modified Primer

| Primers | | | Amplicon | primer dimer |
|---|---|---|---|---|
| Upstream | Downstream | Enzyme | $\Delta C_T$ | $C_T$ |
| dA | dC | 40 U ZO5 | 0.0 | 37.0 |
| 2'omeA-2'omeG-2'omeU | dC | 40 U ZO5 | 3.2 | *53 |

The results demonstrate that modified primers that contain modified nucleotides at the three 3' terminal nucleotides are useful in the present methods.

We claim:

1. A kit for carrying out a nucleic acid amplification reaction, wherein said kit comprises a pair of primers, wherein a least one primer of said pair contains a modified nucleotide within the three 3' terminal nucleotide positions; wherein said modified nucleotide is selected from the group consisting of 2'-O-methyl nucleotides, 2'-fluoro-nucleotides, 2'-amino nucleotides, and arabinose nucleotides.

2. The kit of claim 1, wherein said modified nucleotide is a 2'-O-methyl nucleotide.

3. The kit of claim 1, wherein said modified nucleotide is a 2'-fluoro-nucleotide.

4. The kit of claim 1, wherein said modified nucleotide is a 2'-amino nucleotide.

5. The kit of claim 1, wherein said modified nucleotide is an arabinose nucleotide.

6. The kit of claim 2, wherein said modified nucleotide is at the 3' terminal position.

7. The kit of claim 3, wherein said modified nucleotide is at the 3' terminal position.

8. The kit of claim 4, wherein said modified nucleotide is at the 3' terminal position.

9. The kit of claim 5, wherein said modified nucleotide is at the 3' terminal position.

10. A kit of claim 1, wherein each primer of said pair of primers independently contains a modified nucleotide within the three 3' terminal nucleotide positions; wherein said modified nucleotide is selected from the group consisting of 2'-O-methyl nucleotides, 2'-fluoro-nucleotides, 2'-amino nucleotides, and arabinose nucleotides.

11. A method for amplifying a nucleic acid target sequence, wherein said method comprises carrying out a primer-based amplification reaction in a reaction mixture comprising a pair of primers, wherein a least one primer of said pair contains a modified nucleotide within the three 3' terminal nucleotide positions; wherein said modified nucleotide is selected from the group consisting of 2'-O-methyl nucleotides, 2'-fluoro-nucleotides, 2'-amino nucleotides, and arabinose nucleotides.

12. The method of claim 11, wherein said modified nucleotide is a 2'-O-methyl nucleotide.

13. The method of claim 11, wherein said modified nucleotide is a 2'-fluoro-nucleotide.

14. The method of claim 11, wherein said modified nucleotide is a 2'-amino nucleotide.

15. The method of claim 11, wherein said modified nucleotide is an arabinose nucleotide.

16. The method of claim 12, wherein said modified nucleotide is at the 3' terminal position.

17. The method of claim 13, wherein said modified nucleotide is at the 3' terminal position.

18. The method of claim 14, wherein said modified nucleotide is at the 3' terminal position.

19. The method of claim 15, wherein said modified nucleotide is at the 3' terminal position.

20. A method of claim 11, wherein each primer of said pair of primers independently contains a modified nucleotide within the three 3' terminal nucleotide positions; wherein said modified nucleotide is selected from the group consisting of 2'-O-methyl nucleotides, 2'-fluoro-nucleotides, 2'-amino nucleotides, and arabinose nucleotides.

* * * * *